United States Patent
Castillo et al.

(10) Patent No.: US 7,497,843 B1
(45) Date of Patent: Mar. 3, 2009

(54) SYRINGE INTERFACES, SYRINGE ADAPTERS AND INJECTOR SYSTEMS

(75) Inventors: Luis Castillo, Allison Park, PA (US); James R. Neill, Oakdale, PA (US); Kevin P. Cowan, Allison Park, PA (US)

(73) Assignee: Medrad, Inc., Indianola, PA (US)

( * ) Notice: Subject to any disclaimer, the term of this patent is extended or adjusted under 35 U.S.C. 154(b) by 306 days.

(21) Appl. No.: 11/078,813

(22) Filed: Mar. 11, 2005

Related U.S. Application Data

(60) Provisional application No. 60/552,962, filed on Mar. 12, 2004.

(51) Int. Cl.
*A61M 1/00* (2006.01)
(52) U.S. Cl. .................................................. 604/152
(58) Field of Classification Search ........... 64/151–155, 64/228, 187
See application file for complete search history.

(56) References Cited

U.S. PATENT DOCUMENTS

| | | | |
|---|---|---|---|
| 4,006,736 A | | 2/1977 | Kranys et al. |
| 4,677,980 A | * | 7/1987 | Reilly et al. ............. 600/432 |
| 5,383,858 A | | 1/1995 | Reilly et al. |
| 5,520,653 A | | 5/1996 | Reilly et al. |
| 5,873,861 A | | 2/1999 | Hitchins et al. |
| 5,944,694 A | * | 8/1999 | Hitchins et al. ............. 604/154 |
| 5,947,935 A | * | 9/1999 | Rhinehart et al. .......... 604/218 |
| 6,017,330 A | | 1/2000 | Hitchins et al. |
| 6,312,410 B1 | | 11/2001 | Yamamoto |
| 6,322,535 B1 | * | 11/2001 | Hitchins et al. ............. 604/154 |
| 6,569,127 B1 | * | 5/2003 | Fago et al. .................. 604/218 |
| 6,652,489 B2 | | 11/2003 | Trocki et al. |
| 6,726,657 B1 | | 4/2004 | Dedig et al. |
| 6,984,222 B1 | | 1/2006 | Hitchins et al. |
| 7,018,363 B2 | | 3/2006 | Cowan et al. |
| 2002/0177811 A1 | * | 11/2002 | Reilly et al. ............. 604/152 |
| 2003/0045789 A1 | * | 3/2003 | Thompson et al. .......... 600/407 |
| 2004/0064041 A1 | | 4/2004 | Lazzaro et al. |

FOREIGN PATENT DOCUMENTS

| | | |
|---|---|---|
| JP | 9122234 | 5/1997 |
| WO | WO 0108727 | 2/1977 |
| WO | WO 0137903 | 5/2001 |

* cited by examiner

*Primary Examiner*—Kevin C Sirmons
*Assistant Examiner*—Elizabeth R MacNeill
(74) *Attorney, Agent, or Firm*—Jill Denesvich; Gregory L. Bradley

(57) ABSTRACT

A syringe interface is provided for attaching a syringe to an injector. The syringe includes, a first and second set of generally opposing, radially outward projecting mounting flanges, and a second set of flanges offset from the first set of mounting flanges. The syringe interface includes a first set of generally opposed slots adapted to receive therethrough the first set and second set, respectively, of mounting flanges, and a first and second set of generally opposed retaining flanges adapted to releasably engage the first and second set respectively, a set of mounting flanges, when the syringe is rotated within the syringe interface. The syringe verification mechanism includes at least one flange interaction element disposed within at least one slot of the first set of slots, and at least a first flange abutment member being positioned to prevent engagement of the second set of mounting flanges with the second set of retaining flanges unless the flange verification element interacts with at least one of the flanges of the first set of mounting flanges.

15 Claims, 9 Drawing Sheets

Fig. 3A
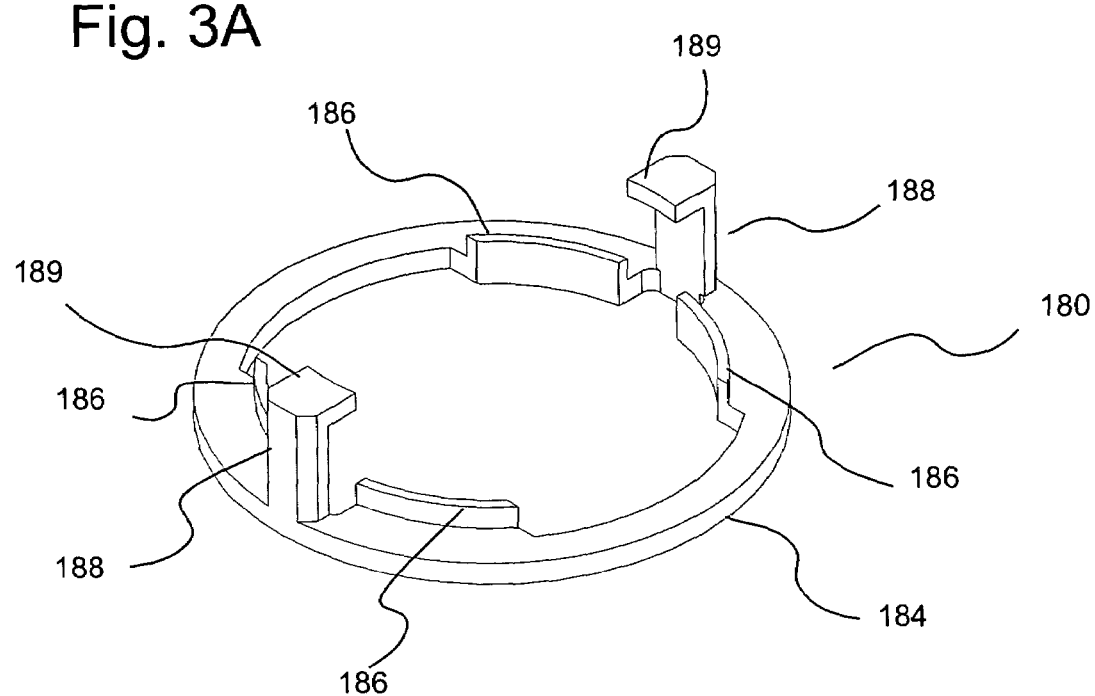
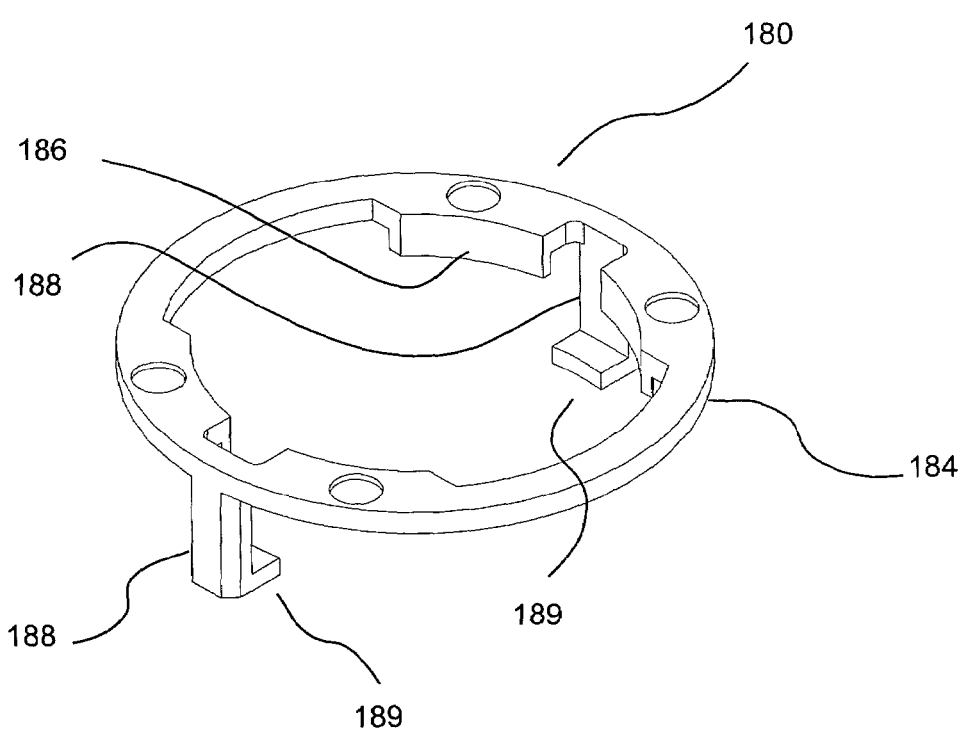
Fig. 3B

SYRINGE INTERFACES, SYRINGE ADAPTERS AND INJECTOR SYSTEMS

CROSS-REFERENCE TO RELATED APPLICATION

This application claims benefit of U.S. Provisional Patent Application Ser. No. 60/552,962, filed Mar. 12, 2004, the disclosure of which is incorporated herein by reference.

BACKGROUND OF THE INVENTION

The present invention relates generally to syringe interfaces, syringe adapters and injectors and, more particularly, to syringe interfaces, syringe adapters and injectors for use in injection of a fluid into a patient.

Injector-actuated syringes and powered injectors are used in medical procedures such as angiography, computed tomography, ultrasound and NMR/MRI. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

The front-loading injector of U.S. Pat. No. 5,383,858 includes a bayonet syringe mounting mechanism for securing the syringe to the front wall of the injector. In that regard, the syringe of U.S. Pat. No. 5,383,858 includes two generally opposed mounting flanges on a rearward end of the syringe which cooperate with corresponding retaining flanges on the injector thereof to form a bayonet connection.

U.S. Pat. No. 5,873,861 discloses another front-loading, bayonet-type syringe mounting mechanism in which multiple pairs or sets of syringe mounting flanges cooperate with corresponding pairs of injector retaining flanges to mount a syringe upon an injector. In one embodiment, a first pair of mounting flanges are offset from at least a second pair of mounting flanges. For example, the first pair of mounting flanges can be offset from the second pair of mounting flanges by approximately 90°. Use of multiple pairs of mounting flanges and, particularly offset pairs of mounting flanges, can, for example, assist in distributing forces experienced by a syringe during an injection procedure. Such flange configurations can thereby allow use of certain syringe manufacturing materials at higher pressures than previously attainable or the use of relatively low-strength materials not otherwise usable with high pressure-syringe and injector designs without the use of a pressure jacket.

Other types of mounting mechanisms for front-loading syringes are disclosed in PCT Publication No. WO 01/37903 and U.S. Pat. No. 6,652,489, each assigned to the assignee of the present invention, the disclosures of which are incorporated herein by reference.

In general, the use of specifically designed mounting mechanisms on front-loading injectors prevents the use of syringes of various other types (that is, syringes having a mounting mechanism not directly compatible with the syringe interface/retaining mechanism of the front-loading injector) with the front-loading injectors. Syringe adapters attachable to front-loading injectors are sometimes used to allow the use of such syringes with front-loading injectors.

For example, U.S. Pat. No. 5,520,653 discloses several adapters designed to allow the use of various syringes with a front-loading injector. Another adapter for allowing use of various syringes with a front-loading injector is disclosed in Japanese Patent Publication No. 09-122234. Other adapters are disclosed, for example, in PCT Publication No. WO 01/08727 and U.S. patent application Ser. No. 09/633,299, filed on Aug. 8, 2000, each assigned to the assignee of the present invention, the disclosures of which are incorporated herein by reference.

Although a number of syringe interfaces and adapters are currently available, it remains desirable to develop improved syringe interfaces and adapters for use with syringes of various types.

SUMMARY OF THE INVENTION

A syringe interface is provided for attaching a first syringe to an injector. The first syringe includes a main body, a plunger movably disposed within the main body, a first set of generally opposing, radially outward projecting mounting flanges, and a second set of generally opposing, radially outward projecting mounting flanges, the first set of mounting flanges being offset from the second set of mounting flanges. The syringe interface includes a first set of generally opposed slots adapted to receive therethrough the first set of mounting flanges, a second set of generally opposed slots adapted to receive therethrough the second set of mounting flanges, the first set of slots being offset from the second set of slots, a first set of generally opposed retaining flanges adapted to releasably engage the first set of mounting flanges, a second set of generally opposed retaining flanges adapted to releasably engage the second set of mounting flanges when the syringe is rotated within the syringe interface to bring the first set of mounting flanges into general alignment with the first set of retaining flanges and the second set of mounting flanges into general alignment with the second set of retaining flanges, and a syringe verification mechanism. The syringe verification mechanism includes at least one flange interaction element disposed within at least one slot of the first set of slots, and at least a first flange abutment member in operative connection with the flange verification element, the first flange abutment member being positioned to prevent engagement of the second set of mounting flanges with the second set of retaining flanges unless the flange verification element interacts with at least one of the flanges of the first set of mounting flanges.

In one embodiment, the flange verification element includes a contact member that is movably disposed within at least one slot of the first set of slots. The contact member can, for example, be slidably disposed in an axial direction within the at least one slot and the first flange abutment member can be in mechanical connection with the contact member.

The first flange abutment member can include a first contact member slidably disposed in an axial direction within the at least one slot of the first set of slots. The syringe verification mechanism can further include a second contact member slidably disposed in an axial direction within the other slot of the first set of slots. The first contact member and the second contact member can, for example, project forward from an annular member that is slidably disposed within the syringe interface. The second contact member can be positioned with respect to the annular member generally opposite to the first contact member.

The syringe interface can further include a plunger abutment adapted to contact a plunger of a third syringe during attachment of the third syringe to the syringe interface. The syringe interface can also include a plunger interface slidably disposed within the plunger abutment. In one embodiment, the plunger abutment comprises a generally cylindrical member. The plunger interface can include at least two radially outward extending connection flanges on a forward end thereof that cooperate with at least two relatively flexible capture members protruding from the rear of the plunger. The flexible capture members flex when contacted by the connection flanges to form a connection with the plunger interface.

The piston interface can further include at least two sloped surfaces to the rear of the connecting flanges at an axial position in general alignment with the axial position of a radially inward projecting flange on the rearward end of each of the flexible capture members when the plunger is connected to the plunger interface. The radius of each of sloped surfaces can increase around the circumference thereof until the radius of each of the sloped surfaces is at least equal to the radius of one of the connecting flanges. In one embodiment, upon rotation of the plunger relative to the piston interface, the flexible capture members are flexed outwardly by contact of the radially inward extending flanges of the flexible capture member with the sloped surfaces until the radially inward extending flanges can pass forward of the connecting flanges of the piston interface, thereby enabling detachment of the plunger from the plunger interface.

In another aspect, the present invention provides an adapter for connecting a first syringe to an injector including an injector syringe interface adapted to connect a second to the injector. The first syringe includes an elongated main body, a plunger movably disposed within the main body, at least a first set of generally opposing, radially outward projecting mounting flanges, and at least a second set of generally opposing, radially outward projecting mounting flanges. The first set of mounting flanges is offset from the second set of mounting flanges. The adapter includes an injector interface adapted to connect the adapter to the injector syringe interface and a syringe interface adapted to connect the first syringe to the adaptor. The syringe interface includes a first set of generally opposed slots adapted to receive therethrough the first set of mounting flanges and a second set of generally opposed slots adapted to receive therethrough the second set of mounting flanges. The first set of slots are offset from the second set of slots. The syringe interface also includes a first set of generally opposed retaining flanges adapted to releasably engage the first set of mounting flanges and a second set of generally opposed retaining flanges adapted to releasably engage the second set of mounting flanges when the syringe is rotated within the syringe interface to bring the first set of mounting flanges into general alignment with the first set of retaining flanges and the second set of mounting flanges into general alignment with the second set of retaining flanges. The syringe interface further includes a syringe verification mechanism including at least one flange interaction element disposed within at least one slot of the first set of slots and at least a first flange abutment member in operative connection with the flange verification element. The first flange abutment member is positioned to prevent engagement of the second set of mounting flanges with the second set of retaining flanges unless the flange verification element interacts with at least one of the flanges of the first set of mounting flanges.

In a further aspect, the present invention provides an injector system including a first syringe including a main body; a plunger slidably disposed within the main body; a first set of generally opposing, radially outward projecting mounting flanges; and a second set of generally opposing, radially outward projecting mounting flanges. The first set of mounting flanges are offset from the second set of mounting flanges. The injector system also includes an injector including a drive member adapted to impart force to the syringe plunger and a syringe interface as described above adapted to connect the first syringe to the injector.

In another aspect, another embodiment of a syringe interface for attaching a first syringe to an injector is provided. The first syringe includes a main body, a plunger slidably disposed within the main body and a mounting mechanism associated with the main body. The syringe interface includes a retaining mechanism adapted to cooperate with the mounting mechanism of the first syringe, and a plunger abutment extending forward to a predetermined axial position and adapted to contact a plunger of a second syringe during attachment of the second syringe to the syringe interface, the plunger of the second syringe being at an axial position within the second syringe further rearward than the axial position of the plunger within the first syringe.

The syringe interface can further include a plunger interface that operates to transfer force between the injector and the plunger. In one embodiment, the plunger interface is slidably disposed within the plunger abutment. The plunger interface can include at least two radially outward extending connection flanges on a forward end thereof that cooperate with at least two relatively flexible capture members protruding from the rear of the plunger. The flexible capture members flex when contacted by the connection flanges to form a connection with the plunger interface. The piston interface can further include at least two sloped surfaces to the rear of the connecting flanges at an axial position in general alignment with the axial position of a radially inward projecting flange on the rearward end of each of the flexible capture members when the plunger is connected to the plunger interface. The radius of each of sloped surfaces can increase around the circumference thereof until the radius of each of the sloped surfaces is at least equal to the radius of one of the connecting flanges.

In still a further aspect, the present invention provides a syringe interface for attaching a first syringe to an injector. The first syringe includes a main body, a plunger slidably disposed within the main body and a mounting mechanism associated with the main body. The syringe interface includes: a retaining mechanism adapted to cooperate with the mounting mechanism of the first syringe and a plunger interface adapted to transfer force from the injector to the plunger. The plunger interface includes at least two radially outward extending connection flanges on a forward end thereof that cooperate with at least two relatively flexible capture members protruding from the rear of the plunger. The flexible capture members flex when contacted by the connection flanges to form a connection with the plunger interface. The piston interface includes at least two sloped surfaces to the rear of the connecting flanges at an axial position in general alignment with the axial position of a radially inward projecting flange on the rearward end of each of the flexible capture member when the plunger is in connection with the plunger interface. The radius of each of sloped surfaces increases around the circumference thereof until the radius of each of the sloped surfaces is at least equal to the radius of one of the connecting flanges such that, upon rotation of the plunger relative to the piston interface, the flexible capture members are flexed outwardly by contact of the radially inward extending flanges of the flexible capture member with the sloped surfaces until the radially inward extending flanges can pass forward of the connecting flanges of the piston interface, thereby enabling detachment of the plunger from the plunger interface.

The present invention, along with further aspects and attendant advantages, will best be understood by reference to the following detailed description taken in conjunction with the accompanying drawings.

BRIEF DESCRIPTION OF THE DRAWINGS

FIG. 3A illustrates a front perspective view of an embodiment of a syringe verification mechanism of the syringe interface of FIG. 1A.

FIG. 3B illustrates a rear perspective view of the syringe verification mechanism of FIG. 3A.

DETAILED DESCRIPTION OF THE INVENTION

The syringe interfaces, adapters and injectors of the present invention are particularly suited for use with prefilled syringes as disclosed, for example, in U.S. Pat. No. 5,873,861, which are designed to contain an injection fluid for extended periods of time prior to an injection procedure. There are significant advantages in the use of syringes pre-filled with injection fluid. For example, use of a prefilled syringe saves the user time, minimizes the potential for mis-labeling of the liquid medium, minimizes the potential of contamination of the liquid medium and also minimizes the possibility of injecting air into the patient.

As discussed, for example, in U.S. Pat. No. 5,873,861, the material from which a prefilled syringe is fabricated is preferably chemically and biochemically compatible with the injection fluid for extended periods of time. The construction material(s) for the syringe should preferably exhibit good barrier properties, for example, low water vapor transmission rate, because changes in moisture content can detrimentally affect the ionic character of certain injection fluids. Moreover, unlike syringes designed to be filled after mounting on a powered injector, prefilled syringes containing injection fluid must be sterilized. Therefore, the construction material(s) for the syringe should also exhibit physical characteristics suitable to withstand the pressures, temperatures and other forces experienced during sterilization, such as autoclave sterilization. Further, like all syringes used in connection with powered injectors, the material of the syringe must have physical characteristics suitable to withstand pressure and other forces experienced during injection. Finally, it is desirable that the syringe material be clear so that the injection fluid contained in the syringe can be viewed.

While certain materials exhibit suitable long-term chemical and biochemical compatibility characteristics, such materials have often been found to be structurally weaker (that is, to have lower tensile strength and/or lower elasticity) than materials commonly used in front-loading, syringes used without pressure jackets. The syringes of U.S. Pat. No. 5,873,861 include multiple pairs of mounting flanges to enable fabrication of those syringes from a variety of fabrication materials (for example, polypropylene) to withstand the forces experienced in typical motorized injector applications.

Figure 1A:
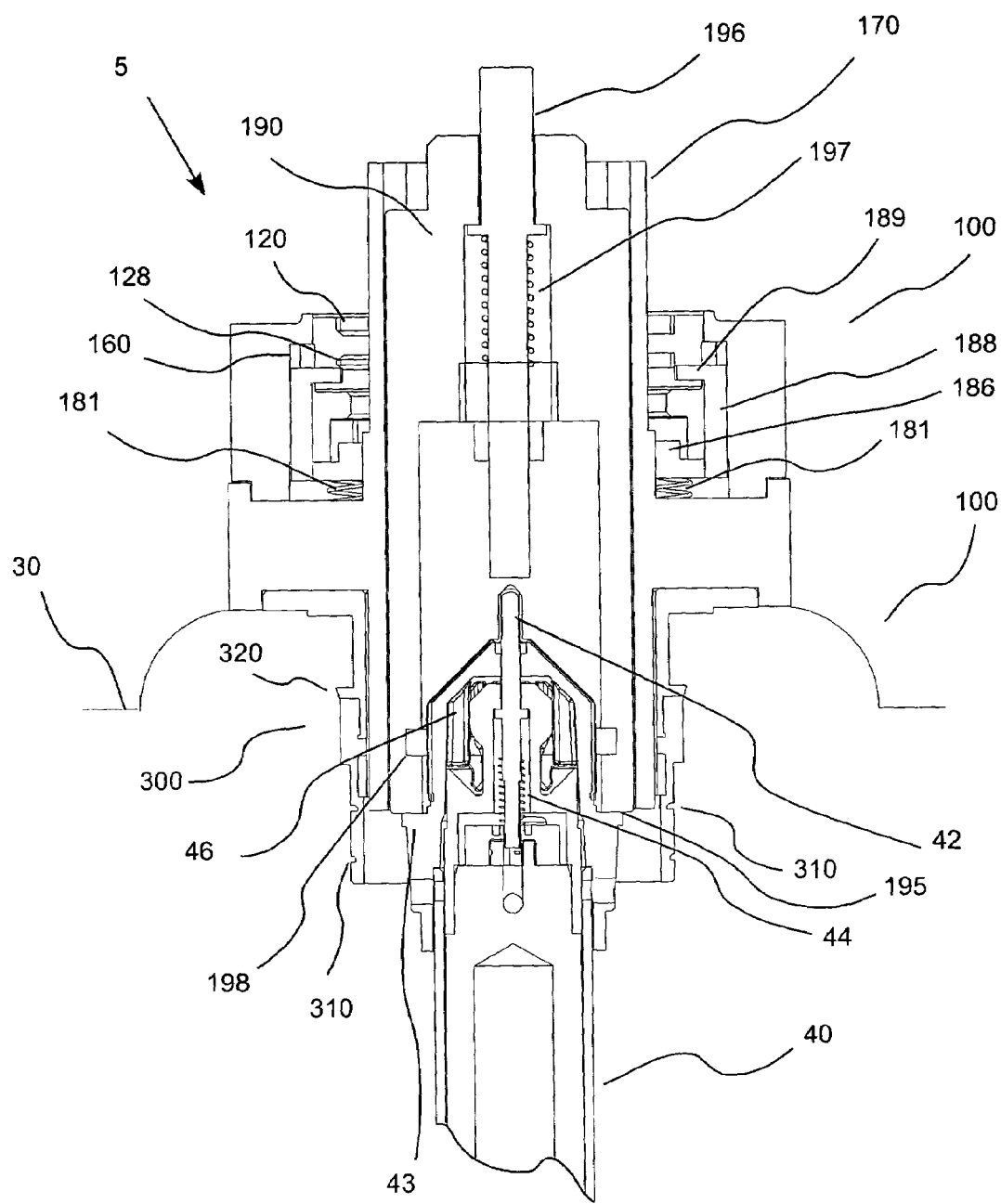
FIG. 1A illustrates a cutaway view of an embodiment of an injector system of the present invention in which a syringe interface or adapter is attached to a powered injector.
Figure 1B:
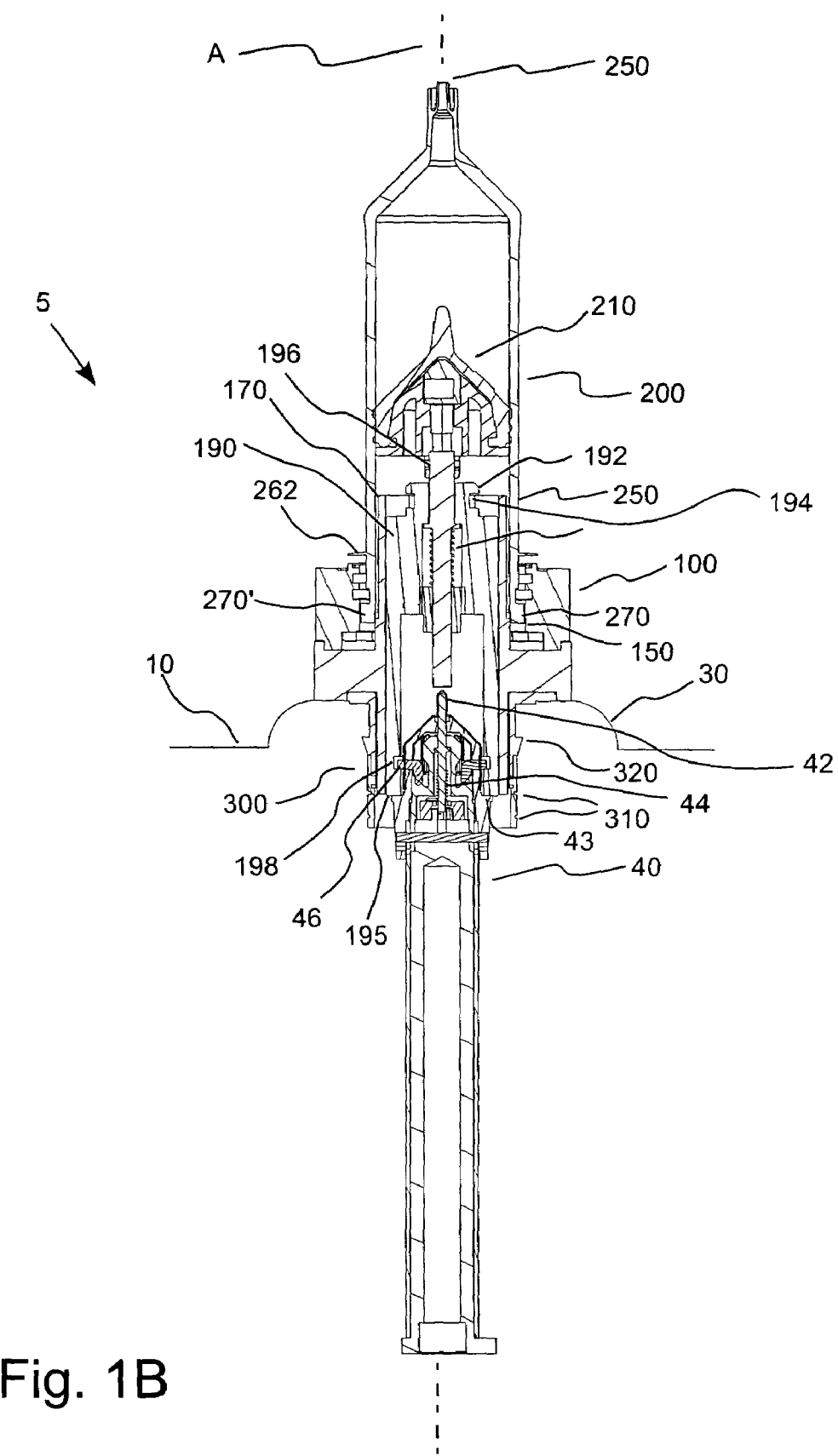
FIG. 1B illustrates a cross-sectional view of the injector system of FIG. 1A wherein a syringe is partially inserted into the syringe interface of the syringe adapter and in which the system has been rotated about its axis by approximately 90° as compared to the view of FIG. 1A.

An embodiment of a front-loading injector system 5 of the present invention is illustrated in, for example, FIGS. 1A and 1B. Injector system 5 includes a powered injector 10 and at least one syringe 200 for injection of, for example, a contrast medium for use in a medical imaging procedure. Injector housing 30 of injector 10 preferably includes therein at least a first powered drive member or piston 40 which, for example, cooperates with syringe plunger 210 (via opening or passage 105 formed in a syringe interface or adapter 100 as illustrated, for example, FIG. 1D) to control the movement of plunger 210, which is slidably disposed in syringe 200 to inject a fluid from the interior of syringe 200 into a patient. Multiple syringes can be attached to a single injector by providing, for example, multiple syringe interfaces and multiple drive members associated therewith.

As used herein to describe injection system 5 and other embodiments of the present invention, the terms "axial" or "axially" refer generally to, for example, axis A around which syringe 200 and piston 40 are preferably formed (although not necessarily symmetrically therearound) and to directions collinear with or parallel to axis A. The terms "proximal" or "rearward" refer generally to an axial or a longitudinal direction toward the end of injector housing 30 opposite the end to which syringe 200 is mounted. The terms "distal" or "forward" refer generally to an axial or a longitudinal direction toward a syringe tip 250 (from which pressurized fluid exits syringe 200). The term "radial" refers generally to a direction normal to an axis such as axis A.

Figure 4B:
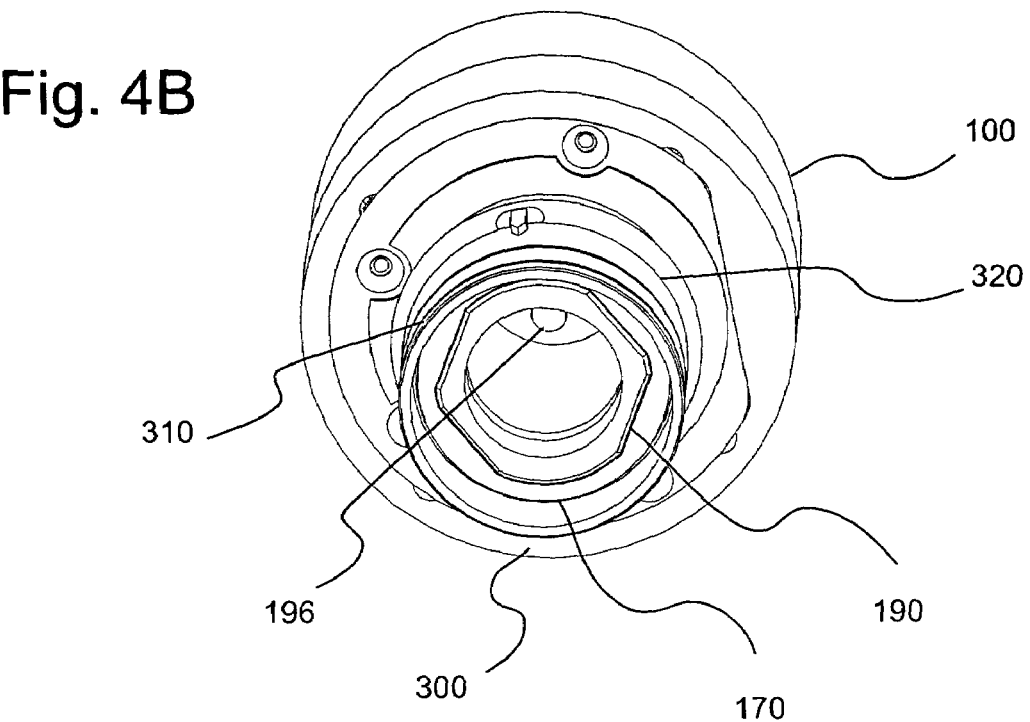
FIG. 4B illustrates a rear perspective view of the assembled syringe adapter of the injector system of FIG. 1A.
Figure 4A:
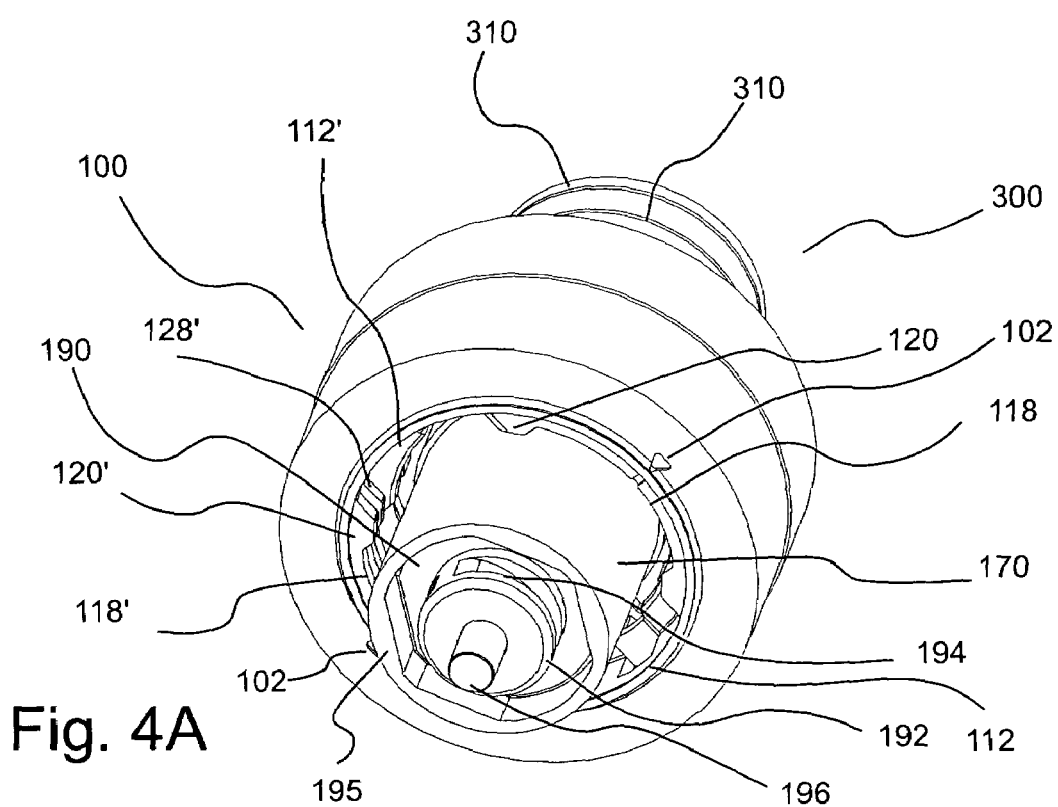
FIG. 4A illustrates a front perspective view of the assembled syringe adapter of the injector system of FIG. 1A.

In a number of respects, syringe interface or adapter 100 of injector system 5 operates in a manner similar to the operation of the syringe interface illustrated, for example, in FIGS. 1B and 3B of U.S. Pat. No. 5,873,861. In that regard, as illustrated, for example, in FIGS. 1D and 4A, opening 105 of syringe interface 100 includes around the circumference thereof two pairs of opposed, axially extending slots 112 and 112' and 118 and 118'. The centers of first pair of slots 112 and 112' are positioned or rotated approximately 90° from the centers of second pair of slots 118 and 118'. Slots 112 and 112' separate and define at least a first pair of radially inwardly projecting syringe retaining flanges 120 and 120' formed around the circumference of the opening 105. To the rear of first retaining flanges 120 and 120' is a first circumferential groove or channel 124, which is in communication with the axial slots 112 and 112'.

To the rear of channel 124, are a second pair of radially inwardly projecting retaining flanges 128 and 128'. Retaining flanges 128 and 128' are generally aligned with retaining flanges 120 and 120'. A second circumferential channel 130 (also in communication with slots 112 and 112') is formed between the rear of mounting flanges 128 and 128' and the forward surfaces of a third pair of retaining flanges 140 and 140'. A third circumferential channel 150 is formed to the rear of mounting flanges 140 and 140'.

Slots 118 and 118' are formed in retaining flanges 120 and 120' and 128 and 128'. Preferably, the depth of slots 118 and 118' is somewhat less that the radial width of retaining flanges 120 and 120'. Slots 118 and 118' preferably separate and frame third pair of radially inwardly projecting syringe retaining flanges 140 and 140' formed around the circumference of opening 105 as discussed above.

Figure 1C:
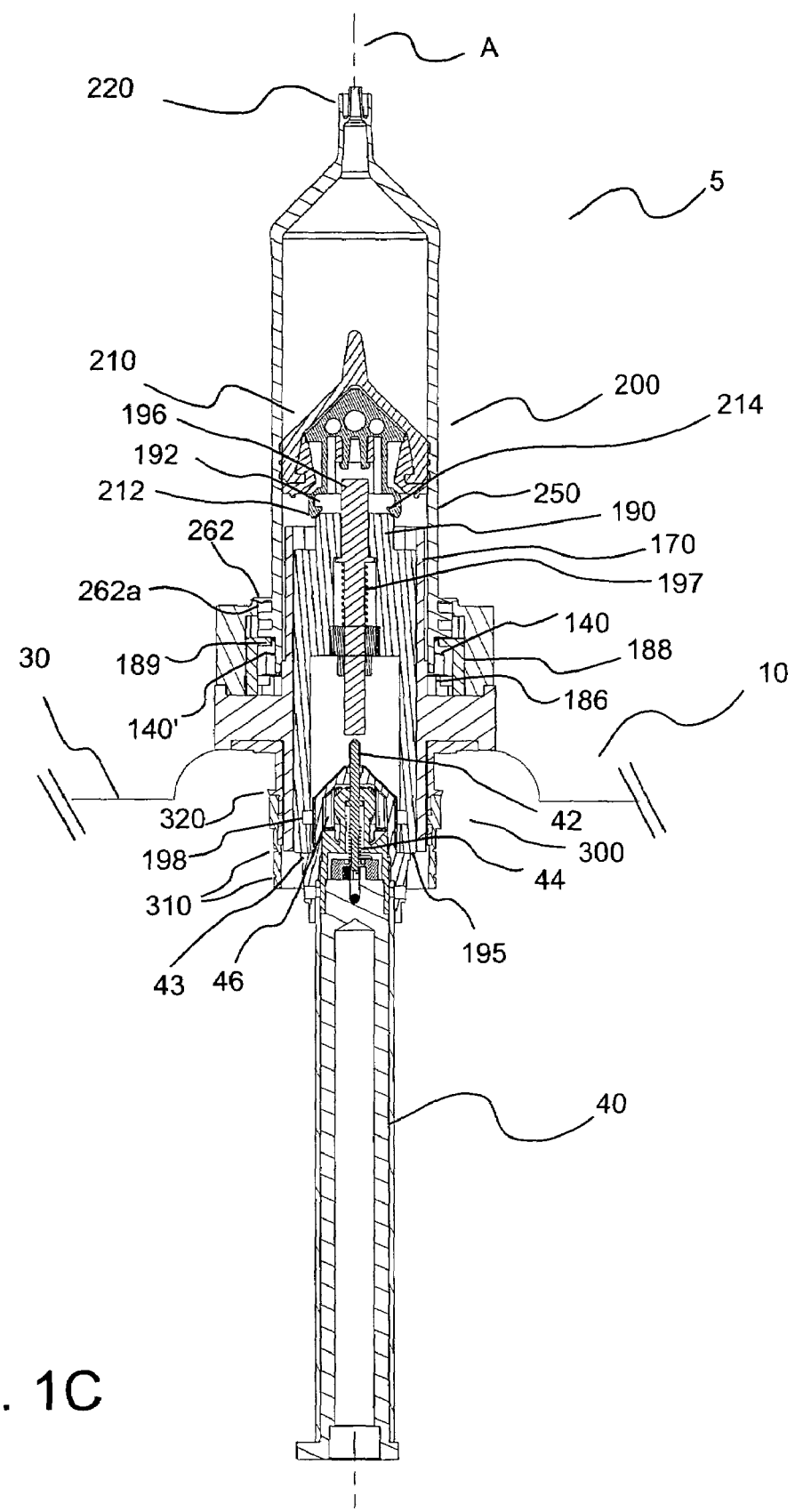
FIG. 1C illustrates another cross-sectional view of the injectors system of FIG. 1A in the same orientation of FIG. 1A in which the syringe has been inserted to its rearward most position in the syringe interface of the syringe adapter.
Figure 1D:
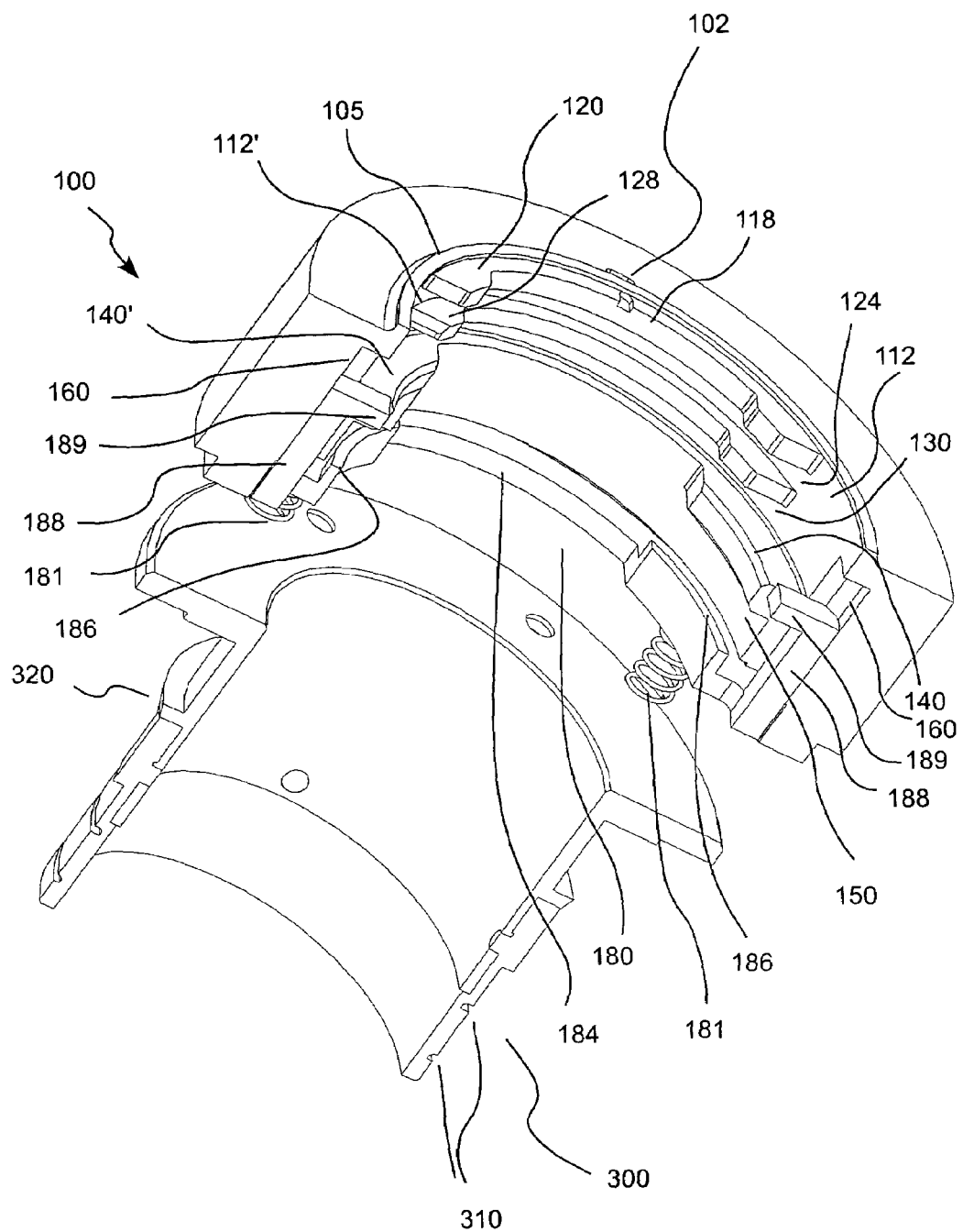
FIG. 1D illustrates a cutaway, perspective view of the syringe adapter of FIG. 1A.
Figure 2:
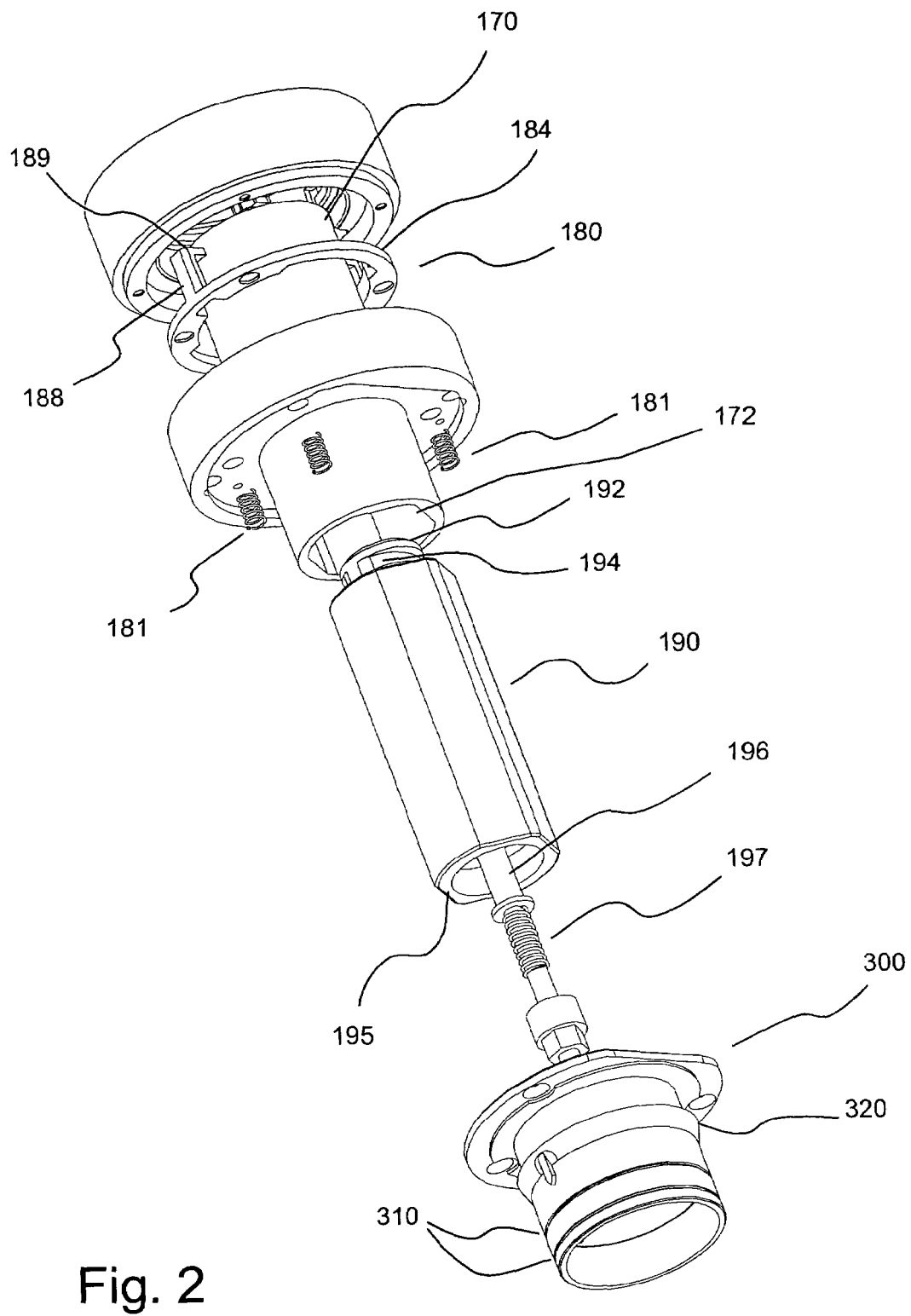
FIG. 2 illustrates a rear perspective, exploded or disassembled view of the syringe adapter of the injector system of FIG. 1A.
Figure 5A:
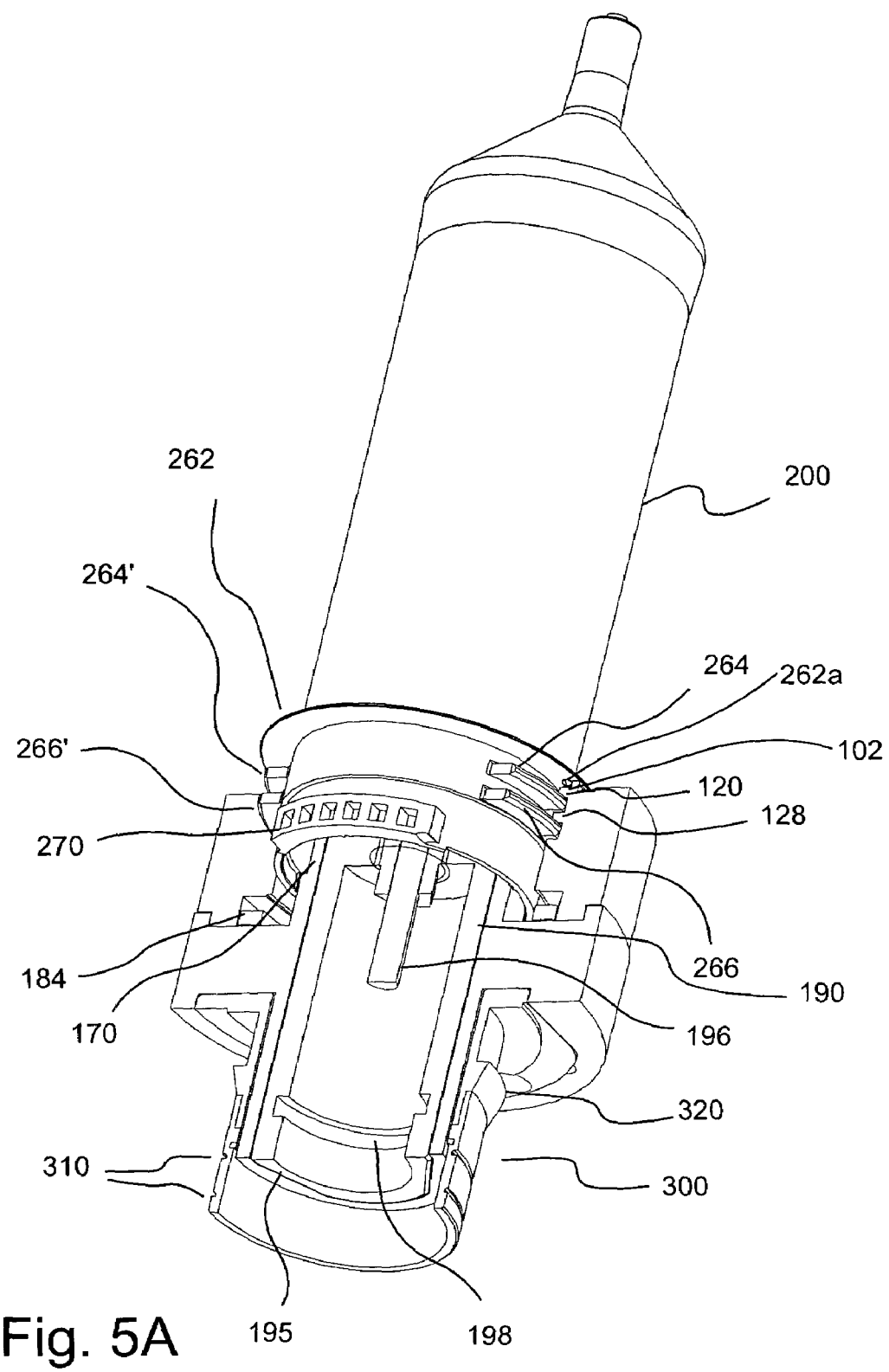
FIG. 5A illustrates a perspective, partially cutaway view of a syringe attached to the syringe adapter of FIG. 1A.
Figure 5B:
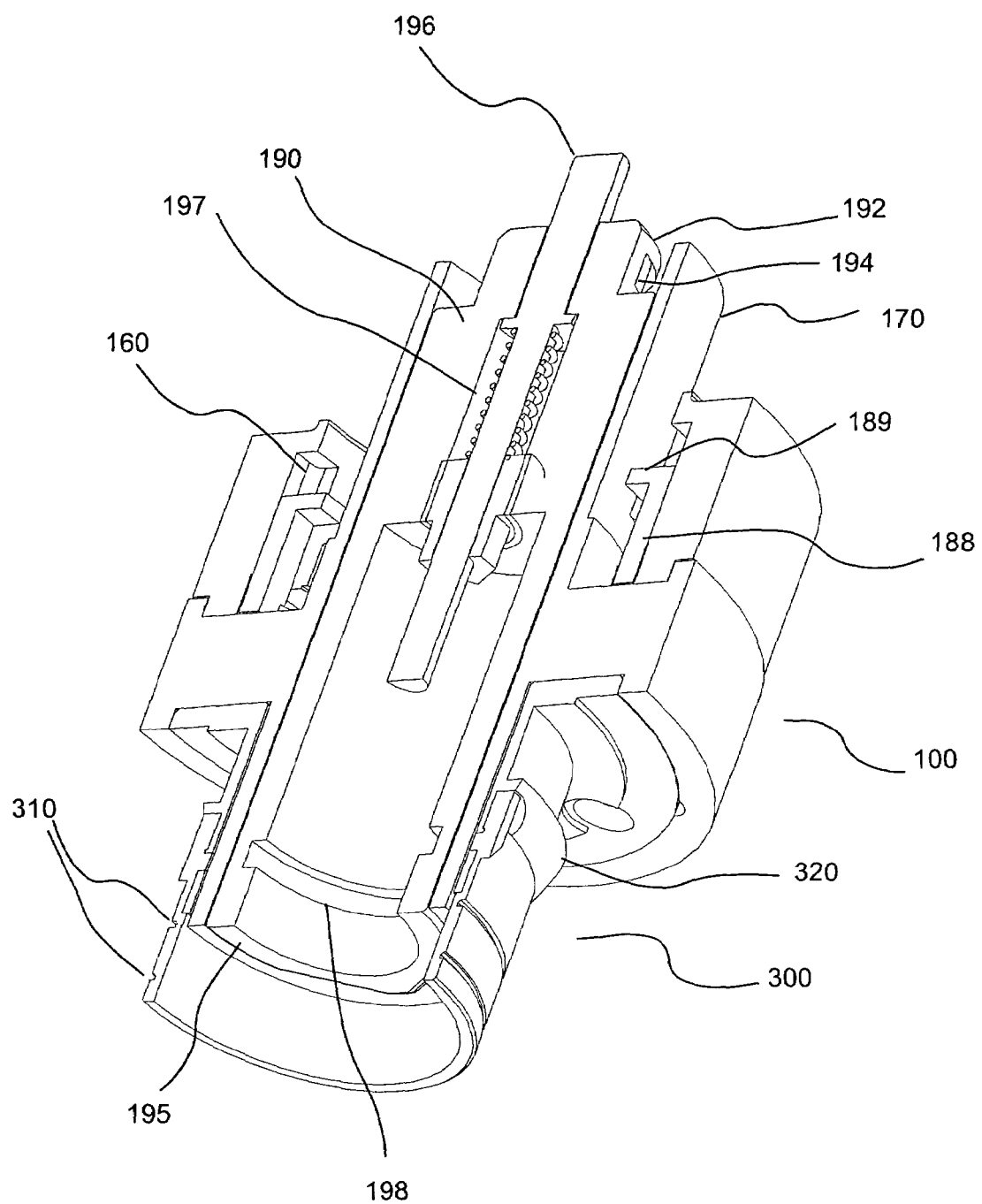
FIG. 5B illustrates a perspective, cutaway view of the syringe adapter of FIG. 1A

Syringe 200 includes a body 220 having a rear portion which includes a first pair of radially extending mounting flanges 264 and 264' and a second pair of radially extending mounting flanges 266 and 266' (see, for example, FIGS. 1C and 5A). A radially extending drip flange 262 can be formed forward of first mounting flanges 264 and 264' on body 250. First mounting flanges 264 and 264' and second mounting flanges 266 and 266' are in general alignment. The structure of second mounting flanges 266 and 266' is generally similar to the structure of first mounting flanges 264 and 264'.

Syringe body 220 also preferably includes a third pair of radially extending mounting flanges 270 and 270'. The centers of third mounting flanges 270 and 270' are offset or rotated around the circumference of syringe body 250 approximately 90° (around axis A) from the centers of first mounting flanges 264 and 264'.

Opening 105 receives and firmly secures syringe 200 to syringe interface 100 and thereby to injector 10. During mounting, third pair of mounting flanges 270 and 270' pass through second pair of slots 118 and 118', respectively. First pair of mounting flanges 264 and 264' and second pair of mounting flanges 266 and 266' pass through first pair of slots 112' and 112, respectively. Upon, for example, abutment of drip flange 262 with the front wall of syringe interface 100, syringe 200 is fully rearwardly seated with syringe interface 100, and syringe 200 is rotated clockwise relative to syringe interface 100 approximately 90° to firmly and releasably mount syringe 200 on injector housing 30 of injector 10. A mechanical stop can be provided (for example, a radially inward projecting abutment in one or more of channels 124, 130 or 150) to prevent over-rotation of syringe 200. Moreover, an audible click (or other indication) of proper rotation/full engagement of syringe 200 within syringe interface 100 can be provided. In the embodiment of FIGS. 1A through 5B, for example, tabs 262a project rearward from flange 262 and seat within depressions 102 on a forward face of syringe interface 100 to cause an audible click when syringe 200 is fully/properly engaged with syringe interface 100. To release syringe 200 from injector 20, the process of mounting is simply reversed.

In the embodiment of FIGS. 1A through 5B, syringe interface 100 includes a verification mechanism including a contact member 180 that is slidably biased (for example, via springs 181) within syringe interface 100. When a syringe 200 is moved rearward into syringe interface 100, flanges 266 and 266' contact radially inward extending contacts or flanges 189 of contact member 180 (see, for example, FIGS. 1C, 3A and 3B) causing contact member 180 to move rearward within syringe interface 100 to the position illustrated in FIG. 1C, once syringe 200 is moved to its rearward most position within syringe interface 100. Contact member 180 further includes a base ring 184 from which extending members or extensions 188 extend axially forward. Mounting flanges 189 extends radially inward from the forward end of axial extensions 188. Mounting flange abutment members 186, positioned on each side of extensions 188 in the embodiment of FIGS. 1A through 5, also extend axially forward from base ring 184. When contact member 180 is biased in its forward position as illustrated, for example, in FIG. 1A, flange abutment members 186 extend axially forward into circumferential channel 150.

When a rearward portion of syringe 200 is inserted into opening 105 of syringe interface 100, mounting flanges 270 and 270' pass through slots 118 and 118', while generally aligned mounting flange sets 264 and 264' and 266 and 266' pass through slots 112 and 112'. Mounting flanges 266 and 266' contact a forward surface of contact or abutment members 189 of contact member 180. Contact of flanges 266 and 266' with contact or abutment members 189 causes contact member 180 to move rearward within syringe interface 10, thereby causing flange abutment members 186 to move out of channel 150 and allowing mounting flanges 270 and 270' to be rotated within channel 150 to align with retaining flanges 140 and 140' (to fully engage syringe 200 with syringe interface 100). In the embodiment of FIGS. 1 through 5B, axially extending members 188 are slidably disposed within slots or channels 160 formed in syringe interface 100. Channels 160 prevent contact member 180 from rotating relative to syringe interface 100.

Verification mechanism 180 described above operates mechanically. It is apparent to one skilled in the art that the verification mechanism can operate in another manner, for example, electromechanically. In that regard, sensors (for example, switches, optical sensors etc.) as known in the art can be positioned within one or more of the slots of syringe interface 100 to ensure that one or more mounting flanges corresponding to mounting flanges 264, 264', 266, 266', 270 or 270' are present upon a syringe.

Syringe interface 100 further includes a generally cylindrical core member or abutment member 170 disposed within syringe interface 100. In the embodiment of FIGS. 1A through 5B, abutment member 170 extends into the interior of syringe 200 (see, for example, FIGS. 1B and 1C) to a predetermined axial position within syringe 200.

In the embodiment of FIGS. 1A through 5B, slidably disposed within core member or abutment member 170, is a plunger interface 190 that operates to transfer force between drive member 40 and plunger 210. Plunger interface 190 includes a forward portion including a plunger attachment having one or more radially outward extending flanges 192 that cooperates with rearward projecting flex legs 212 of plunger 210 to releasably attach plunger interface 190 to plunger 210. The operation of flex legs 212 is described, for example, in U.S. Pat. Nos. 5,873,861 and 5,947,935, assigned to the assignee of the present invention, the disclosures of which are incorporated herein by reference. In general, as plunger 210 is moved rearward relative to plunger interface 190 (or plunger interface 190 is move forward relative to plunger 210), flex legs 212 contact flanges 192 and flex radially outward to a stressed state to allow further rearward movement of plunger 210 relative to plunger interface 190. Once ledges or flanges 214 formed on flex legs 212 pass rearward of the rearward surfaces of flanges 192, flex legs 212 snap or otherwise return inward engage flanges 192 of plunger interface 190.

To facilitate disconnection of plunger interface 190 from plunger 210, plunger interface 190 includes, to the rear of flanges 192, sloped surfaces 194. The radii of sloped surfaces 194 increase around the circumference thereof until the radii are at least equal to the radii of flanges 192. During connection of plunger 210 to plunger interface 190, plunger interface 190 is aligned about its axis relative to the alignment of plunger 210 about its axis so that flex legs 212 are aligned with an area of sloped surfaces 194 of reduced radius to allow radially inward projecting flanges 216 of flex legs 212 to be in a inward position in which ledges 214 abut a rearward surface of flanges 192. In this position, plunger 210 cannot be moved axially forward relative to plunger interface 190. To allow disengagement of plunger interface 190 from connection with plunger 210, syringe 200 (and thereby plunger 210) is rotated relative to plunger interface 190 so that flanges 216 travel along sloped surfaces 194, gradually forcing flex legs 212 to a radially outward position until ledges 214 no longer abut a rearward surface of flanges 192 and plunger 210 can be move axially forward relative to plunger interface 190 for disconnection therefrom.

Flanges 192 can be appropriately axially positioned and rotated about axis A to an appropriate position such that a secure engagement is formed between plunger 210 and plunger interface 190 at the same time that syringe 200 engages with syringe interface 100. In that regard, when syringe 200 is moved axially rearward to fully seat within syringe interface 100, the rearward surfaces of flanges 192 are preferably generally aligned to engage ledges 214. Further, when syringe 200 is rotated about its axis to align mounting flanges on the syringe with retaining flanges on syringe interface 100 as described above, flanges 214 of flex legs 212 are generally aligned with areas of sloped surfaces 194 of reduced radius to allow flanges 216 to be in a radially inward positions in which ledges 214 abut the rearward surfaces of flanges 192 as illustrated, for example, in FIG. 1C. To prevent plunger interface 190 from rotating relative to syringe interface 100 when syringe 100 is rotated, plunger interface 190 is, in the embodiment of FIGS. 1A through 5B, formed to have a non-circular shape (for example, the shape of a hexagon), which cooperates with a corresponding non-circular (for example, hexagonal) shaped passage 172 (see, for example, FIG. 2) formed in core 170.

In an alternative embodiment, a sensing system is provided to signal the control system of injector 10 a known amount of time before flange 192 is engaged by flex legs 212 so that the control system stops advancement of piston 40 after a secure connection is made between plunger interface 190 and plunger 210, but before piston 40 is advanced to a degree to cause injection of fluid from the interior of syringe 200. A sensing system for "auto docking" of a piston to a syringe plunger is described generally, for example, in U.S. patent application Ser. No. 10/159,592, filed May 30, 2002, assigned to the assignee of the present invention, the disclosure of which incorporated herein by reference.

In the embodiment of FIGS. 1A through 5B, plunger interface 190 includes a biased sensing pin 196 (biased, for example via a spring 197) slidably disposed therein. Sensing pin 196 extends forward of the forward surface of flanges 192. Sensing pin 196 is in operative connection with a biased sensing pin 42 (for example, spring-loaded via spring 44) projecting from piston 40. As piston 40 (and thereby plunger interface 190) is advanced forward toward plunger 210 sensing pin 196 contacts a rearward or inward surface of plunger 210. Sensing pin 196 transfers the resultant force to pin 42, and pin 42 is forced rearward so that it, for example, impinges upon the field of a sensor such as an optical sensor (not shown). As described above, the sensor can signal the control system of injector 10 so that the control system stops advancement of piston 40 after a predetermined amount of time or distance of advancement of piston 40, so that piston 40 is brought into operative engagement with plunger 210 (via intermediate plunge interface 190), but advancement of piston 40 is stopped before movement of syringe plunger 210. The amount of time between such a signal and the cessation of piston movement can, for example, depend on compliance or tolerance within the piston drive mechanism and plunger interface 190 as well as the type of syringe attached to interface 100.

Piston 40 can, for example, include retractable pins 46 that form an abutting connection with one or more ledges, flanges or grooves 198 formed around the interior circumference of plunger interface 190 when piston 40 is to be retracted, thereby causing plunger interface 190 (and, thereby, syringe plunger 210) to retract or move rearward along with piston 40.

During advancement of piston 40 to engage plunger 210, as well as during advancement of piston 40 to advance plunger 210 within syringe 200 (for example, to expel air or injection fluid contained within syringe 100), pins 46 are preferably in a retracted state. In this state, a forward facing surface 43 of piston 40 abuts a rearward surface 195 of plunger interface 190 during forward movement of piston 40 to force plunger interface 190 (and thereby plunger 210) forward. As described above and in U.S. patent application Ser. No. 10/159,592, if retraction of plunger 210 is desired, pins 46 are extended to abut ledge 198.

Syringe interface 100 can, for example, be connected directly to or be an integral part of an injector. In the embodiment of FIGS. 1A through 5B, however, syringe interface 100 includes or is in operative connection with an adaptive section including a connector 300 for releasably engaging syringe interface 100 with an injector. Adaptive section, connector or injector interface 300 for use with syringe interface 100 of the present invention allows the use of syringe 200 with many different types of injectors originally designed for use with syringes having an injector interface, mounting mechanism or connector different from that of syringe 200. In the embodiment of FIGS. 1A through 5B, flange 320 of connector 300 described above, for example, is designed to cooperate with a front-loading injector and release mechanism as described, in at least one embodiment, in PCT Publication No. WO 01/37903 and U.S. Pat. No. 6,652,489, each assigned to the assignee of the present invention, the disclosures of which are incorporated herein by reference. In the embodiment of FIGS. 1A through 5B, flange 320 encompasses the entire circumference of injector connector 300.

The rearward end of connector 300 includes indicators 310 that can cooperate with a light source and sensors to provide information about the configuration of syringe interface 100, as described in U.S. patent application Ser. No. 09/765,498, filed on Jan. 18, 2001, assigned to the assignee of the present invention, the disclosure of which is incorporated herein by reference.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. A syringe interface for attaching a first syringe to an injector, the first syringe comprising an elongated main body, a plunger movably disposed within the main body, a first set of generally opposing, radially outward projecting mounting flanges, and a second set of generally opposing, radially outward projecting mounting flanges, the first set of mounting flanges being offset from the second set of mounting flanges, the syringe interface comprising:

a first set of generally opposed slots adapted to receive therethrough the first set of mounting flanges;

a second set of generally opposed slots adapted to receive therethrough the second set of mounting flanges, the first set of slots being offset from the second set of slots;

a first set of generally opposed retaining flanges adapted to releasably engage the first set of mounting flanges;

a second set of generally opposed retaining flanges adapted to releasably engage the second set of mounting flanges when the syringe is rotated within the syringe interface to bring the first set of mounting flanges into general alignment with the first set of retaining flanges and the second set of mounting flanges into general alignment with the second set of retaining flanges; and a syringe verification mechanism comprising:
at least one extension disposed within at least one slot of the first set of slots and axially forward of the second set of generally opposed retaining flanges; and
at least a first flange abutment member in operative connection with the at least one extension, the first flange abutment member being positioned to prevent engagement of the second set of mounting flanges with the second set of retaining flanges unless the at least one extension interacts with at least one of the flanges of the first set of mounting flanges, wherein the first flange abutment member comprises a first contact member slidably disposed in an axial direction within the at least one slot of the first set of slots, wherein the syringe verification mechanism further comprises a second contact member slidably disposed in an axial direction within the other slot of the first set of slots, wherein the first contact member and the second contact member project forward from an annular member that is slidably disposed within the syringe interface.

2. The syringe interface of claim 1 wherein the at least one extension comprises a contact member that is movably disposed within at least one slot of the first set of slots.

3. The syringe interface of claim 2 wherein the contact member is slidably disposed in an axial direction within the at least one slot and the first flange abutment member is in mechanical connection with the contact member.

4. The syringe interface of claim 1 wherein the second contact member is positioned with respect to the annular member generally opposite to the first contact member.

5. The syringe interface of claim 1, further comprising a plunger abutment adapted to contact a plunger of the first syringe during attachment of the first syringe to the syringe interface.

6. The syringe interface of claim 5, further comprising a plunger interface slidably disposed within the plunger abutment.

7. The syringe interface of claim 5 wherein the plunger abutment comprises a generally cylindrical member.

8. The syringe interface of claim 6 wherein the plunger interface comprises at least two radially outward extending connection flanges on a forward end thereof that cooperate with at least two relatively flexible capture members protruding from the rear of the plunger, the flexible capture members flexing when contacted by the connection flanges to form a connection with the plunger interface.

9. The syringe interface of claim 8 wherein the piston interface further comprises at least two sloped surfaces to the rear of the connecting flanges at an axial position in general alignment with the axial position of a radially inward projecting flange on the rearward end of each of the flexible capture members when the plunger is connected to the plunger interface, the radius of each of sloped surfaces increasing around the circumference thereof until the radius of each of the sloped surfaces is at least equal to the radius of one of the connecting flanges.

10. The syringe interface of claim 9 wherein upon rotation of the plunger relative to the piston interface, the flexible capture members are flexed outwardly by contact of the radially inward extending flanges of the flexible capture member with the sloped surfaces until the radially inward extending flanges can pass forward of the connecting flanges of the piston interface, thereby enabling detachment of the plunger from the plunger interface.

11. The syringe interface of claim 1 further including:
an injector interface operatively disposed at the reward end of the syringe interface; indicators disposed on a rearward end of the injector interface.

12. An adapter for connecting a first syringe to an injector comprising an injector syringe interface adapted to connect a second syringe to the injector, the first syringe comprising an elongated main body, a plunger movably disposed within the main body, at least a first set of generally opposing, radially outward projecting mounting flanges, and at least a second set of generally opposing, radially outward projecting mounting flanges, the first set of mounting flanges being offset from the second set of mounting flanges, the adapter comprising:

an injector interface adapted to connect the adapter to the injector syringe interface; and a syringe interface adapted to connect the first syringe to the adaptor, the syringe interface comprising:
a first set of generally opposed slots adapted to receive therethrough the first set of mounting flanges;
a second set of generally opposed slots adapted to receive therethrough the second set of mounting flanges, the first set of slots being offset from the second set of slots;
a first set of generally opposed retaining flanges adapted to releasably engage the first set of mounting flanges;
a second set of generally opposed retaining flanges adapted to releasably engage the second set of mounting flanges when the syringe is rotated within the syringe interface to bring the first set of mounting flanges into general alignment with the first set of retaining flanges and the second set of mounting flanges into general alignment with the second set of retaining flanges; and
a syringe verification mechanism comprising:
at least one extension disposed within at least one slot of the first set of slots and axially forward of the second set of generally opposed retaining flanges; and
at least a first flange abutment member in operative connection with the at least one extension, the first flange abutment member being positioned to prevent engagement of the second set of mounting flanges with the second set of retaining flanges unless the at least one extension interacts with at least one of the flanges of the first set of mounting flanges, wherein the first flange abutment member comprises a first contact member slidably disposed in an axial direction within the at least one slot of the first set of slots, wherein the syringe verification mechanism further comprises a second contact member slidably disposed in an axial direction within the other slot of the first set of slots, wherein the first contact member and the second contact member project forward from an annular member that is slidably disposed within the syringe interface.

13. The adapter of claim 12 wherein the injector interface includes indicators adapted to cooperate with a light source and sensors.

14. A injector system comprising:
a first syringe comprising:
    a main body;
    a plunger slidably disposed within the main body;
    a first set of generally opposing, radially outward projecting mounting flanges; and
    a second set of generally opposing, radially outward projecting mounting flanges, the first set of mounting flanges being offset from the second set of mounting flanges;
an injector comprising a drive member adapted to impart force to the syringe plunger; and
a syringe interface adapted to connect the first syringe to the injector, the syringe interface comprising:
    a first set of generally opposed slots adapted to receive therethrough the first set mounting flanges;
    a second set of generally opposed slots adapted to receive therethrough the second set of mounting flanges, the first set of slots being offset from the second set of slots;
    a first set of generally opposed retaining flanges adapted to releasably engage the first set of mounting flanges;
    a second set of generally opposed retaining flanges adapted to releasably engage the second set of mounting flanges when the syringe is rotated within the syringe interface to bring the first set of mounting flanges into general alignment with the first set of retaining flanges and the second set of mounting flanges into general alignment with the second set of retaining flanges; and
    a syringe verification mechanism comprising:
        at least one extension disposed within at least one slot of the first set of slots and axially forward of the second set of generally opposed retaining flanges; and
        at least a first flange abutment member in operative connection with the at least one extension, the first flange abutment member being positioned to prevent engagement of the second set of mounting flanges with the second set of retaining flanges unless the at least one extension interacts with at least one of the flanges of the first set of mounting flanges,
    wherein the first flange abutment member comprises a first contact member slidably disposed in an axial direction within the at least one slot of the first set of slots,
    wherein the syringe verification mechanism further comprises a second contact member slidably disposed in an axial direction within the other slot of the first set of slots,
    wherein the first contact member and the second contact member project forward from an annular member that is slidably disposed within the syringe interface.

15. The injector system of claim 14 further including:
an injector interface operatively disposed at the reward end of the syringe interface;
indicators disposed on a rearward end of the injector interface.

* * * * *

UNITED STATES PATENT AND TRADEMARK OFFICE
CERTIFICATE OF CORRECTION

PATENT NO. : 7,497,843 B1  Page 1 of 1
APPLICATION NO. : 11/078813
DATED : March 3, 2009
INVENTOR(S) : Luis Castillo, James R. Neill and Kevin P. Cowan It is certified that error appears in the above-identified patent and that said Letters Patent is hereby corrected as shown below:

ON THE TITLE PAGE
In Item (58), under "Field of Classification Search", in Column 1, Lines 1-2,
delete "64/151-155, 64/228, 187" and insert -- 604/151-155, 604/228, 187 --, therefor.

IN THE DRAWINGS
In Fig. 1A, Sheet 1 of 9, below Tag "181" delete Tag "100" and insert Tag -- 30 --, therefor.

IN THE SPECIFICATION
In Column 5, Line 40, delete "1A" and insert -- 1A. --, therefor.
In Column 8, Line 13, delete "10," and insert -- 100, --, therefor.

IN THE CLAIMS
In Column 13, Line 4, in Claim 14, delete "A" and insert -- An --, therefor.
In Column 13, Line 21, in Claim 14, after "set" insert -- of --.

Signed and Sealed this

Seventeenth Day of August, 2010

David J. Kappos
*Director of the United States Patent and Trademark Office*